United States Patent [19]
Park et al.

[11] Patent Number: 5,872,249
[45] Date of Patent: Feb. 16, 1999

[54] 3-AMMONIOPROPENYL CEPHALOSPORIN COMPOUNDS AS ANTIBACTERIAL AGENTS AND PROCESS FOR PREPARING THE SAME

[75] Inventors: Hokoon Park; Yong Sup Lee; Jae Yeol Lee; Dae Hwan Suk; Eun-Rhan Woo, all of Seoul, Rep. of Korea

[73] Assignee: Korea Institute of Science and Technology, Seoul, Rep. of Korea

[21] Appl. No.: 941,772

[22] Filed: Sep. 30, 1997

Related U.S. Application Data

[62] Division of Ser. No. 522,792, Sep. 1, 1995, Pat. No. 5,675,003.

[51] Int. Cl.$^6$ .................... C07D 501/18; C07D 501/24
[52] U.S. Cl. .................... 540/225; 540/222; 540/224
[58] Field of Search ................................ 540/225

[56] References Cited

U.S. PATENT DOCUMENTS

| | | | |
|---|---|---|---|
| 4,278,671 | 7/1981 | Ochiai et al. | 424/246 |
| 4,912,212 | 3/1990 | Ochiai et al. | 540/227 |
| 5,675,003 | 10/1997 | Park et al. | 540/225 |

FOREIGN PATENT DOCUMENTS

| | | |
|---|---|---|
| 0 462 009 A1 | 12/1991 | European Pat. Off. . |
| 0 528 343 A2 | 2/1993 | European Pat. Off. . |
| 54-154786 | 12/1979 | Japan . |

OTHER PUBLICATIONS

Naito et al., "Sythesis and Structure–Activity Relationships of a New Series of Cephalosporins, BMY–28142 and Related Compounds", *J. of Antibiotics*, 8:1092–1107 (Aug., 1986).

*Drugs of the Future*, 13:369–371 (1988).

Kamachi et al., "Synthesis of a New Series of Cephalosporins Having 3–Substituted–Ammonio–1–Propenyl Group as the C–3 Side Chain", *J. of Antibiotics*, 5:533–543 (May, 1990).

*Primary Examiner*—Mukund J. Shah
*Assistant Examiner*—Pavanaram K. Sripada
*Attorney, Agent, or Firm*—Townsend and Townsend and Crew

[57] ABSTRACT

A 3-ammoniopropenyl cephalosporin of the following formula (I):

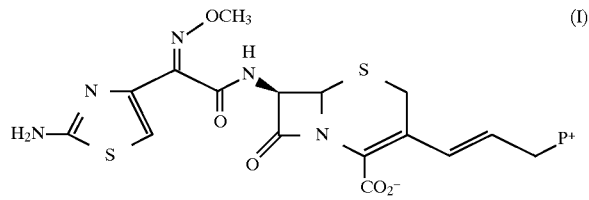

wherein P is hydroxylated alicyclic or aliphatic amines such as meso-3,4-dihydroxy-1-methylpyrrolidine, (3S,4S)-3,4-dihydroxy-1-methylpyrrolidine, (3R,4R)-3,4-dihydroxy-1-methylpyrrolidine, rac-3,4-trans-dihydroxy-1-methylpyrrlidine, (2S,4R)-4-hydroxy-1-methyl-2-pyrrolidinemethanol, N-methyl-bis(2-hydroxyethyl)amine, 3,4-cis-dihydroxy-1-methylpiperidine, 3,4-trans-dihydroxypiperidine, 4-hydroxy-1-methylpiperidine, 2-hydroxymethyl-1-methylpiperidine, or tropine, or a pharmaceutically acceptable salt thereof, exhibits good antibacterial activities against a wide variety of Gram-positive and Gram-negative bacteria; and a process for the preparation thereof.

3 Claims, No Drawings

3-AMMONIOPROPENYL CEPHALOSPORIN COMPOUNDS AS ANTIBACTERIAL AGENTS AND PROCESS FOR PREPARING THE SAME

This is a division of application Ser. No. 08/522,792 filed Sep. 1, 1995 now U.S. Pat. No. 5,675,003, the disclosure of which is incorporated by reference.

BACKGROUND OF THE INVENTION

1. Field of the invention

The present invention relates to novel 3-propenyl quaternary ammonium cephalolosporins with hydroxylated alicyclic or aliphatic amines useful as anti-bacterial agents. The present invention also provides a process for the preparation thereof.

2. Description of the Prior Art

Japanese Laid-Open Patent Publication No. 54-154,786 described the preparation of pyridiniomethyl cephalosporin (ceftazidime). Ceftazidime exhibits a potent anti-pseudomonal activity. However, it is less active against staphylococci and Enterobacter cloacae P99. Thereafter many quaternary anmmoniomethyl cephalosporin derivatives such as cefpirome (Drugs of the Future, 13, 369–371 (1988)), and cefepime (German Patent No. 3,307,550) were developed. Cefepime is an aminothiazolyl cephalosporin derivative having an aliphatic ammonium group at the C-3 position and was prepared from 7-ACA and 1-methylpyrrolidine. The detailed synthesis of cefepime is described in *the Journal of Altibiotics*, 1986, 39 (8), 1092~1107. Cefepime exhibits improved anti-staphylococcal activity while retaining high anti-pseudomonal activity.

Particularly, cephem derivatives having an ammoniopropenyl group at the 3-position thereof, which are similar compounds to those of the present invention, have been disclosed in Eur. Pat. 462,009, Eur. Pat. 528,343, and the *Journal of Antibiotics* 1990, 43(5), 533~543.

SUMMARY OF THE INVENTION

The present inventors have found that cephalosporin derivatives having ammoniopropenyl group at the C-3 position thereof and an aminothiazolyl group in the side chain at the 7-position thereof have excellent anti-bacterial activities.

An object of the present invention is therefore to provide novel cephalosporin compounds useful as antibacterial agents; the process for the preparation thereof; and a pharmaceutical composition containing the same.

DETAILED DESCRIPTION OF THE INVENTION

The present invention relates to new 3-ammoniopropenyl cephalosporins having a hydroxylated alicyclic or aliphatic amines of the following formula (I):

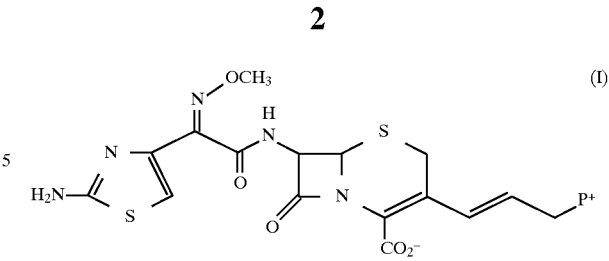

wherein P represents a hydroxylated alicyclic or aliphatic amino group, and a pharmaceutically acceptable salt thereof.

Illustrative examples of the hydroxylated alicyclic or aliphatic amino group represented by P in the formula (I) may be: meso-3,4-dihydroxy-1-methylpyrrolidine, (3S,4S)-3,4-dihydroxy-1-methylpyrrolidine, (3R,4R)-3,4-dihydroxy-1-methylpyrrolidine, rac-3,4-trans-dihydroxy-1-methylpyrrolidine, (2S,4R)-4-hydroxy-1-methyl-2-pyrrolidinemethanol, N-methyl-bis(2-hydroxyethyl)amine, 3,4-cis-dihydroxy-1-methylpiperidine, 3,4-trans-dihydroxypiperidine, 4-hydroxy-1-methylpiperidin, 2 hydroxymethyl-1-methylpiperidine, or tropine.

Non-toxic salts of the compounds of the formula (I), may be their pharmaceutically acceptable salts, for example, alkali metal salts such as sodium salts and potassium salts; tetraethylammonium salts and betain salts; alkaline earth metal salts such as calcium salts and magnesium salts; inorganic salts such as hydrochlorides hydrobromides, hydroiodides, carbonates and bicarbonates; organic carboxylates such as acetates, maleates, lactates and tartrates; organic sulfonates such as methanesulfonates, benzenesulfonates, taurine, and toluenesulfonates; amino acid salts such as arginine salts, lysine salts, serine salts, aspartates and blutamates; amine salts such as trimethylanune salts, pyridine salts, dicyclohexylamine salts, N,N-dibenzylethylenediamine salts, triethanolamine salts, tris (hydroxymethylamino)methane salts and phenethylbenzylamine salts, etc.

The compounds of the present invention exhibit potent anti-bacterial activities against both Gram-positive and Gram-negative bacteria and are useful for treating diseases caused by bacteria.

The new cephalosporins of the formula (I) can be prepared by the following process.

The compounds of the formula (I) and their pharmaceutically acceptable salts can individually be obtained by reacting a compound, which is represented by the following fomula (II):

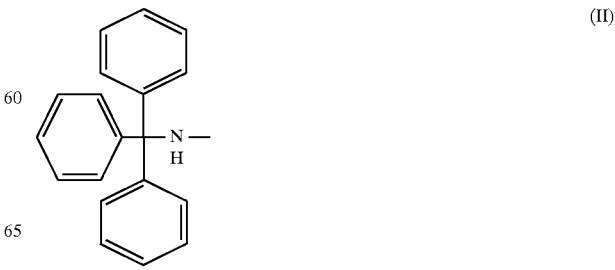

-continued

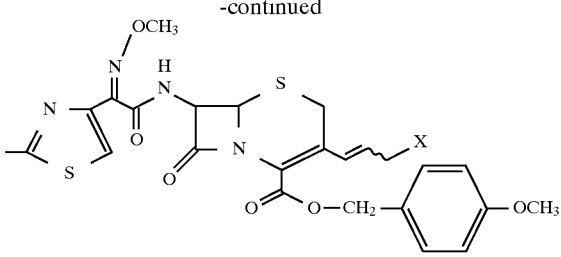

with an amine compound represented by the formula (III) followed by the deprotection of a trityl and p-methoxybenzyl group:

P            (III)

wherein X represents a halogen atom such as an iodine atom, bromine atom or chlorine atom; P represents meso-3,4-dihydroxy-1-methylpyrrolidine, (3S,4S)-3,4-dihydroxy-1-methylpyrrolidine, (3R,4R)-3,4-dihydroxy-1-methylpyrrolidine, rac-3,4-trans-dihydroxy-1-methylpyrrolidine, (2S,4R)-4-hydroxy-1-methyl-2-pyrrolidinemethanol, N-methyl-bis(2-hydroxyethyl)amine, 3,4-cis-dihydroxy-1-methylpiperidine, 3,4-trans-dihydroxypiperidine, 4-hydroxy-1-methylpiperidine, 2-hydroxymethyl-1-methylpiperidine, or tropine.

The conversion of the halogen atom represented by X in the formula (II) into another halogen atom is carried out in a conventional manner. For example, a compound of the formula (II) wherein X represents an iodine atom can be prepared from a compound of the formula (II) wherein X represents a chlorine atom by treating 1 to 5 equivalents of alkali metal iodide such as sodium iodide and potassium iodide in acetone solvent. During the iodination reaction, the compound of the formula (II) is obtained predominantly as the E-isomer.

In the coupling reaction of an amine compound P with a compound represented by the formula (II), the reaction does not proceed effectively in some cases due to the lower solubility of an amine compound P represented by the formula (III) into the reaction solvent. Therefore, the amine compounds P represented by the formula (III) are preferably silylated to improve their solubility in the reaction solvent.

The silylation of an amine compound of the formula (III) by using 2~5 equivalents of silylating agent followed by the reaction with a compound P of the formula (II) is preferable. The preferable silylating reagents are N-methylitrimethylsilyltrifluoroacetamide (MSTFA), Hexamethyldisilazane (HMDS), N,O-bistrimethylsilyltrifluoroacetamide (BSTFA), N,O-bistrimethylsilylacetamide (BSA), bistrimethylsilylurea or N-methylsilylacetamide (MSA). The silylation may be carried out by adding the silylating agent to a solution of an amine compound P represented by formula (III) in the reaction solvent at a reaction temperature of −15° C.~60° C., preferably −15° C.~0°. Usable solvents include acetone; acetonitrile; dimethylsulfoxide; chlorinated hydrocarbons such as dichloromethane, chloroform and carbon tetrachloride; ethers such as ethyl ether, tetrahydrofuran and dioxane; esters such as ethyl acetate; hydrocarbons such as benzene, toluene and xylene; as well as mixed solvents thereof. The preferable solvent is toluene.

The new cephalosporin compound of formula (I) can be prepared by the coupling reaction of the above silylated amine solution with a compound of formula (II) at a reaction temperature of −15° C.~40° C. followed by the removal of the trityl and p-methoxybenzyl group with trifluoroacetic acid. A preferable reaction solvent in the coupling reaction of the above silylated amine solution with a compound of formula (II) is the same as in the silylation reaction of an amine compound of formula (III).

The MICs of the new cephalosporins of the present invention against Gram-positive and Gram-negative bacteria were determined by an in vitro agar dilution method. For comparisons, the MIC values of ceftazidime are also listed.

The new cephalosporins of the present invention exhibited broad and potent antibacterial activities against Gram-positive and Gram-negative bacteria.

Table 1 shows in vitro activity of the new 3-ammoniopropenyl cephalosporins with hydroxylated alicyclic or aliphatic amines.

TABLE

In vitro antimicrobial activity of the cephalosporins (I) (MIC: μg/ml)

| compound | P | Sp.p 1 | S.p. 2 | S.f. | S.a. 1 | S.a. 2 | S.a. 3 | E.c. 1 | E.c. 2 | E.c. 3 | E.c. 4 | E.c. 5 | Pa. 1 | Pa. 2 | Pa. 3 | Pa. 4 | S.t. | K.o. | K.a. | En.c. 1 | En.c. 2 |
|---|---|---|---|---|---|---|---|---|---|---|---|---|---|---|---|---|---|---|---|---|---|
| 1-a | (meso) | 0.013 | 0.013 | 50 | 0.39 | 0.78 | 0.2 | 0.013 | 0.049 | 0.049 | 0.049 | 0.049 | 3.13 | 3.13 | 1.56 | 0.098 | 0.013 | 3.13 | 0.025 | 6.25 | 0.013 |
| 1-b | (L-) | 0.013 | 0.007 | 50 | 0.39 | 0.78 | 0.2 | 0.025 | 0.049 | 0.025 | 0.049 | 0.049 | 3.13 | 1.56 | 1.56 | 0.098 | 0.025 | 0.78 | 0.025 | 3.13 | 0.013 |
| 1-c | | 0.013 | 0.004 | 50 | 0.39 | 0.78 | 0.2 | 0.013 | 0.049 | 0.025 | 0.049 | 0.049 | 6.25 | 3.13 | 1.56 | 0.2 | 0.025 | 3.13 | 0.049 | 3.13 | 0.013 |
| 1-d | | 0.013 | 0.004 | 50 | | | | 0.013 | 0.049 | 0.013 | 0.098 | 0.049 | 3.13 | 1.56 | 0.78 | 0.098 | 0.025 | 0.78 | 0.025 | 6.25 | 0.013 |
| 1-e | (rac-) | 0.013 | 0.013 | 50 | | | | 0.025 | 0.049 | 0.025 | 0.049 | 0.049 | 6.25 | 3.13 | 1.56 | 0.2 | 0.025 | 3.13 | 0.025 | 6.25 | 0.025 |

TABLE-continued

In vitro antimicrobial activity of the cephalosporins (I) (MIC: μg/ml)

| compound | P | Sp.p 1 | S.p. 2 | S.f. | S.a. 1 | S.a. 2 | S.a. 3 | E.c. 1 | E.c. 2 | E.c. 3 | E.c. 4 | E.c. 5 | Pa. 1 | Pa. 2 | Pa. 3 | Pa. 4 | S.t. | K.o. | K.a. | En.c. 1 | En.c. 2 |
|---|---|---|---|---|---|---|---|---|---|---|---|---|---|---|---|---|---|---|---|---|---|
| 1-f | (piperidinium with OH, OH rac-) | 0.013 | 0.013 | 50 | 0.39 | 0.78 | 0.2 | 0.025 | 0.049 | 0.025 | 0.049 | 0.049 | 3.13 | 1.56 | 0.78 | 0.098 | 0.025 | 3.13 | 0.025 | 12.5 | 0.025 |
| 1-g | (piperidinium with OH) | 0.013 | 0.013 | 50 | 0.39 | 0.78 | 0.2 | 0.025 | 0.049 | 0.049 | 0.098 | 0.049 | 6.25 | 3.13 | 1.56 | 0.2 | 0.049 | 3.13 | 0.025 | 3.13 | 0.025 |
| 1-h | (piperidinium with CH2OH) | 0.013 | 0.007 | 25 | 0.39 | 0.39 | 0.2 | 0.013 | 0.049 | 0.025 | 0.098 | 0.049 | 6.25 | 3.13 | 1.56 | 0.098 | 0.025 | 1.56 | 0.025 | 3.13 | 0.013 |
| 1-I | (bicyclic ammonium with OH) | 0.013 | 0.013 | 50 | 0.39 | 0.78 | 0.2 | 0.025 | 0.049 | 0.025 | 0.098 | 0.049 | 3.13 | 0.78 | 0.39 | 0.2 | 0.049 | 1.56 | 0.025 | 6.25 | 0.025 |
| Celtazidime | | 0.098 | 0.049 | 100 | 12.5 | 12.5 | 3.13 | 0.098 | 0.098 | 0.098 | 0.2 | 0.2 | 3.13 | 0.78 | 0.39 | 0.098 | 0.2 | 0.39 | 0.098 | 100 | 0.025 |

Abbreviations:
S.p. 1, Streptococcus pyrogenes 308 A; S.p. 2, Streptococcus pyrogenes A 77; S.f., Streptococcus faecium MD; S.a. 1, Staphylococcus aureus SG 511; E.c. TEM, S.a. 2, Staphylococcus aureus 285; S.a. 3, Staphylococcus aureus 503; E.c. 1, Escherichia coli O55; E.c. 2, Escherichia coli DC0; E.c. 3, Escherichia coli TEM, E.c. 4, Escherichia coli 1507 E; P.a. 1, Pseudomonas aeruginosa 9027; P.a. 2, Pseudomonas aeruginosa 1592 E; P.a. 3, Pseudomonas aeruginosa 1771; P.a. 4, Pseudomonas aeruginosa 1771 M; S.t., Salmonella typhimurium; K.o., Klebsiella oxytoca 1082E; K.a., Klebsiella aerogenes 1552 E; En.c. 1, Enterobacter cloacao P 99; En.c. 2, Enterobacter cloacae 1321 E.

The spectrum and potency of the activities in most of the compounds are similar to each other. They showed better activities than ceftazidime against Gram-positive organisms including Staphylococcus aureus. Their anti-pseudomonal activities were comparable to ceftazidime. Especially, they exhibited higher activity against Enterobacter cloacae P99, which is resistant to ceftazidime. Accordingly, 3-ammoniopropenyl cephalosporins with hydroxylated alicyclic or aliphatic amines of the general formula (I) were found to be more active and broader in effect than ceftazidime and useful as an anti-bacterial agent.

The following examples which are given without implying limitations show how the invention can be put into practice.

EXAMPLE 1

7β-[2-(2-Aminothiazol-4-yl)-(Z)-2-methoxyiminoacetamido]-3-[(E)-3-(meso-3,4-dihydroxy-1-methyl-1-pyrrolidinio)-1-propen-1-yl]-3-cephem4-carboxylate (I-a)

To a stirred solution of p-methoxybenzyl 7β-[2-(2-tritylaminothiazol-4-yl)-(Z)-2-methoxyiminoacetamido]-3-[(Z)-3-chloro-1-propen-1-yl]-3-cephem-4-carboxylate(300 mg, 0.47 mmol) in acetone (15 mL) was added sodium iodide (165 mg, 1.10 mmol) in one portion at 15°~25° C. After 1 hour, the solvent was evaporated in vacuum and dissolved in ethyl acetate and the mixture was washed with 10% aqueous $Na_2S_2O_4$ solution and brine, successively and then dried. After evaporation of the solvent, the residue was dissolved in toluene (5 ml) and treated with a solution of N-methyltrimethylsilylacetamide (MSTFA, 436 mg, 2.19 mmol) and meso-3,4-dihydroxy-1-methylpyrrolidine (86 mg, 0.73 mmol) in toluene at −10° C. The reaction mixture was kept under refrigeration (ca. −10° C.) for 1 hour. The resulting precipitate was filtered and washed several times with ether to obtain a quaternary ammonium salt as a white solid (ca. 290 mg). The quaternary salt was dissolved in dichloromethane (0.5 ml) and treated with trifluoroacetic acid (1 ml) and anisole (0.5 ml) and stirred for 2 hours at 15°~25° C. The mixture was evaporated and treated with isopropyl ether (20 ml). The resulting solid was washed several times with isopropyl ether and neutralized with saturated aqueous $NaHCO_3$ solution and purified by flash column chromatography (acetonitrile/water=4:1 to 2:1) to provide the desired product as a white solid (74 mg, 38%).

IR (KBr) 3406, 1766, 1602, 1534 $cm^{-1}$.

$^1$H NMR ($D_2O$) δ 7.02 (1H, s), 6.93 (1H, d, J=15.4 Hz), 5.97 (1H, dt, J=15.4, 7.4 Hz), 5.83 (1H, d, J=4.6 Hz), 5.26 (1H, d, J=4.6 Hz), 4.21 (1H, d, J=7.4 Hz), 3.50~4.08 (4H, m), 4.08 (3H, s), 3.87 (2H, s), 3.12 & 3.31 (3H, two s).

EXAMPLE 2

7β-[2-(2-Aminothiazol-4-yl)-(Z)-2-methoxyiminoacetamido]-3-[(E)-3-(3S,4S-dihydroxy-1-methyl-1-pyrrolidinio)-1-propen-1-yl]-3-cephem4-carboxylate (I-b)

The compound was prepared from (3S,4S)-dihydroxy-1-methylpyrrolidine by the same manner described in Example 1. Yield 25%.

IR (KBr) 3400, 1766, 1606, 1534 $cm^{-1}$.

$^1$H NMR ($D_2O$) δ 7.03 (1H, s), 6.93 (1H, d, J=15.1 Hz), 5.97 (1H, m), 5.83 (1H, d, J=4.5 Hz), 5.27 (1H, d, J=4.5 Hz), 4.55 (2H, m), 4.10 (1H, d, J=7.3 Hz), 4.00 (3H, s), 3.65 (2H, s), 3.60~4.05 (4H, m), 3.24 (3H, s).

EXAMPLE 3

7β-[2-(2-Anminothiazol-4-yl)-(Z)-2-methoxyiminoacetamido]-3-[(E)-3-4R-hydroxy-2S-hydroxymethyl-1-methyl-1-pyrrolidinio)-1-propen-1-yl]-3-cephem-4-carboxylate (I-c)

The compound was prepared from (4R)-hydroxy-(2S)-hydroxymethyl-1-methylpyrrolidine by the sarne manner described in Example 1. Yield 28%.

IR (KBr) 3422, 1766, 1606, 1534 $cm^{-1}$.

$^1$H NMR ($D_2O$) δ 7.03 (1H, s), 6.94 (1H, d, J=15.5 Hz), 6.02 (1H, m), 5.84 (1H, d, J=4.6 Hz), 5.28 (1H, d, J=4.6 Hz), 4.30 (1H, m), 4.20 (2H, m), 4.00 (3H, s), 3.06 (3H, s), 2.15~2.50 (2H, m).

EXAMPLE 4

7β-[2-(2-Aminothiazol-4-yl)-(Z)-2-methoxyiminoacetamidol-]3-[(E)-3-bis(2-hydroxyethyl) methylammonio)-1-propen-1-yl]-3 cephem4-carboxylate (I-d)

To a stirred solution of p-methoxybenzyl 7β-[2-(2-tritylaminothiazol-4-yl,-(Z)-2-methoxyiminoacetamido]-3-[(Z)-3-chloro-1-propen-1-yl]-3-cephem-4-carboxylate (457 g, 0.56 mmol) in acetone (15 mL) was added sodium iodide (252 mg, 1.68 mmol) in the portion at 20°~25° C. After 1 hour, the solvent was evaporated in vacuum and dissolved in ethyl acetate and the mixture was washed with 10% aqueous $Na_2S_2O_4$ solution and brine, successively and then dried. After evaporation of the solvent, the residue was dissolved in toluene (5 ml) and treated with a solution of N-methyl-bis(2-hydroxyethyl)amine (131 mg, 1.0 mmol) in toluene (1 ml) at −10° C. The reaction mixture was kept under refrigeration (ca. −10° C.) for 1 hour. The resulting precipitate was filtered and washed several times with ether to obtain a quaternary ammonium salt as a white solid (ca. 290 mg). The quaternary salt was dissolved in dichloromethane (0.5 ml) and treated with trifluoroacetic acid (1 ml) and anisole (0.5 ml) and stirred for 2 hours at 15°~25° C. The mixture was evaporated and treated with isopropyl ether (20 ml). The resulting solid was washed several times with isopropyl ether and neutralized with saturated aqueous $NaHCO_3$ solution and purified by flash column chromatography (acetonitrile/water=4:1 to 2:1) to provide the desired product as a white solid (78 mg, yield 26%).

IR (KBr) 3406, 1766, 1604, 1536 $cm^{-1}$.

$^1$H NMR ($D_2O$) δ 7.05 (1H, s), 6.96 (1H, d, J=15.6 Hz), 5.97 (1H, dt, J=15.6, 7.3 Hz), 5.86 (1H, d, J=4.6 Hz), 5.30 (1H, d, J=4.6 Hz), 4.20 (1H, d, J=7.3 Hz), 4.09 (4H, m), 4.02 (3H, s), 3.73 (2H, s), 3.57 (4H, m), 3.17 (3H, s).

EXAMPLE 5

7β-[2-(2-Aminothiazol-4-yl)-(Z)-2-methoxyiminoacetamido]-3-[(E)-3-(3,4-cis-dihydroxy-1-methyl-1-piperidinio)-1-propen-1-yl]-3-cephem-4-carboxylate (I-e)

The compound was prepared from 3,4-cis-dihydroxy-1-methylpiperidine by the same manner described in Example 1. Yield 26%.

IR (KBr) 3418, 1764, 1606, 1534 $cm^{-1}$.

$^1$H NMR ($D_2O$) δ 7.02 (1H, s), 6.94 (1H, d, J=15.5 Hz), 5.97 (1H, m), 5.83 (1H, d, J=4.9 Hz), 5.28 (1H, d, J=4.9 Hz), 4.15 (2H, m), 2.15~4.12 (8H, m), 3.99 (3H, s) 3.08 & 3.12 (3H, two s).

EXAMPLE 6

7β-[2-(2-Aminothiazol-4-yl)-(Z)-2-methoxyiminoacetamido]-3-[(E)-3-(3,4-trans-dihydroxy-1-methyl-1-piperidinio)-1-propen-1-yl]-3-cephem-4-carboxylate (I-f)

The compound was prepared from 3,4-trans-dihydroxy-1-methylpiperidine by the same manner described in example 4. Yield 49%.

IR (KBr) 3414, 1766, 1604, 1536 cm$^{-1}$.

$^1$H NMR (D$_2$O) δ7.01 (1H, s), 6.93 (1H, d, J=15.5 Hz), 5.95 (1H, m), 5.82 (1H, d, J=4.5 Hz), 5.26 (1H, d, J=4.5 Hz), 4.13 (2H, m), 1.86~4.16 (8H, m), 3.98 (3H, s) 3.03 & 3.15 (3H, two s).

EXAMPLE 7

7β-[2-(2-Aminothiazol-4-yl)-(Z)-2-methoxyiminoacetamido]-3-[(E)-3-(4-hydroxy-1-methyl-1-piperidinio)-1-propen-1-yl]-3-cephem-4-carboxylate (I-g)

The compound was prepared from 4-hydroxy-1-methylpiperidine by the same manner described in EXAMPLE 1. Yield 40%.

IR (KBr) 3414, 1766, 1606, 1536 cm$^{-1}$.

$^1$H NMR (D$_2$O) δ7.09 (1H, s), 6.95 (1H, d, J=15.5 Hz), 6.05 (1H, m), 5.90 (1H, d, J=4.5 Hz), 5.34 (1H, d, J=4.5 Hz), 4.07 (3H, s), 1.95~4.15 (11H, m), 3.08 & 3.11 (3H, two s).

EXAMPLE 8

7β-[2-(2-Aminothiazol-4-yl)-(Z)-2-methoxyiminoacetamido]-3-[(E)-3-(2-hydroxymethyl)-1-methyl-1-piperidinio)-1-propen-1-yl]-3-cephem-4-carboxylate (I-h)

The compound was prepared from 2-hydroxymethyl-1-methylpiperidine by the same manner described in EXAMPLE 1. Yield 28%.

IR (KBr) 3408, 1766, 1604, 1536 cm$^{-1}$.

$^1$H NMR (D$_2$O) δ 7.03 (1H, s), 6.93 (1H, d, J=15.6 Hz), 5.93 (1H, m), 5.83 (1H, d, J=4.6 Hz), 5.27 (1H, d, J=4.6 Hz), 4.62 (1H, m), 4.20 (2H, m), 4.00 (3H, s), 3.70 (3H, s), 1.50~3.93 (10H, m), 3.03 & 3.13 (3H, two s).

EXAMPLE 9

7β-[2-(2-Aminothiazol4-yl)-(Z)-2-methoxyiminoacetamido]-3-[(E)-3-tropinio-1-propen-1-yl]-3-cephem4-carboxylate (I-i)

The compound was prepared from tropine by the same manner described in Example 1. Yield 61%.

IR (KBr) 3422, 1764, 1618, 1534 cm$^{-1}$.

$^1$H NMR (D$_2$O) δ7.03 (1H, s), 6.95 (1H, d, J=15.5 Hz), 5.98 (1H, m), 5.84 (1H, d, J=4.3 Hz), 5.28 (1H, d, J=4.3 Hz), 4.18 (2 H, m), 4.01 (3H, s), 1.95~4.13 (11H, m) (3.03 (3H, two s).

What is claimed is:

1. A process for the preparation of 3-propenyl cephalosporin compound represented by formula (I) which comprises reacting an amine compound of formula (III) with a compound of formula (II):

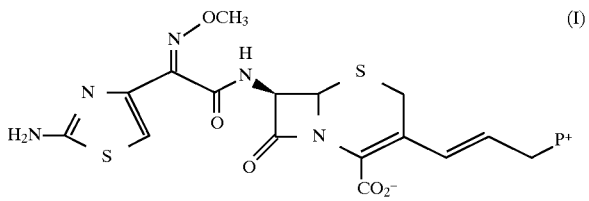

(I)

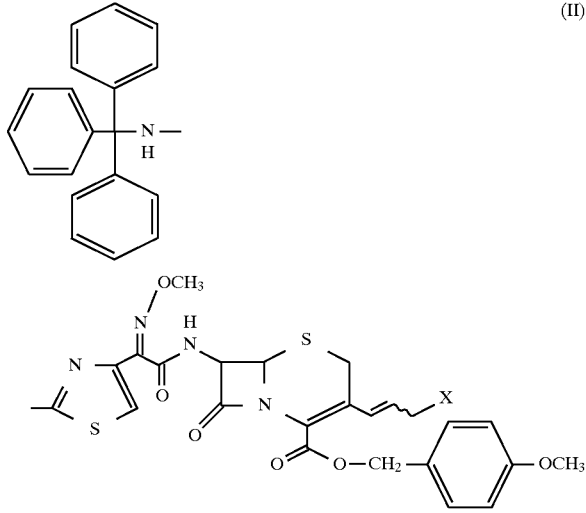

wherein, X is a halogen atom selected from the group consisting of iodine atom, bromine atom and chlorine atom; and P is selected from the group consisting of meso-3,4-dihydroxy-1-methylpyrrolidine, (3S,4S)-3,4-dihydroxy-1-methylpyrrolidine, (3R,4R)-3,4-dihydroxy-1-methylpyrrolidine, rac-3,4-trans-dihydroxy-1-methylpyrrolidine, (2S,4R)-4-hydroxy-1-methyl-2-pyrrolidinemethanol, N-methyl-bis(2-hydroxyethyl)amine, 3,4-cis-dihydroxy-1-methylpiperidine, 3,4-trans-dihydroxy-piperidine, 4-hydroxy-1-methylpiperidine, 2-hydroxymethyl-1-methylpiperidine, and tropine.

2. The process according to claim 1 wherein the amine compound of formula (III) is silylated by using 2~5 equivalents of silylating agents prior to the reaction with the compound of formula (II).

3. The process according to claim 2 wherein the silylating reagent is selected from the group consisting of hexamethyldisilazane (HMDS), N,O-bistrimethylsilyltrifluoroacetamide (BSTFA), N-methyltrimethylsilylacetamide (MSTFA), N,O-bistrimethylsilylacetamide (BSA), bistrimethylsilylurea and N-methylsilylacetamide (MSA).

* * * * *